(12) United States Patent
Huffman (10) Patent No.: US 7,044,734 B2
(45) Date of Patent: May 16, 2006

(54) ENCASED STONE DENTAL MODEL BASE BODY AND METHOD

(76) Inventor: Ronald E. Huffman, 725 Country Wood Way, Sapulpa, OK (US) 74066

( * ) Notice: Subject to any disclaimer, the term of this patent is extended or adjusted under 35 U.S.C. 154(b) by 0 days.

(21) Appl. No.: 09/770,322

(22) Filed: Jan. 26, 2001

(65) Prior Publication Data

US 2002/0102514 A1 Aug. 1, 2002

(51) Int. Cl.
*A61C 11/00* (2006.01)
(52) U.S. Cl. .............................. 433/34; 433/54; 433/60
(58) Field of Classification Search .................. 433/34, 433/54, 60, 64, 213
See application file for complete search history.

(56) References Cited

U.S. PATENT DOCUMENTS

| | | | |
|---|---|---|---|
| 921,791 A | 5/1909 | Benson | |
| 967,086 A | 8/1910 | Tuttle | |
| 1,013,028 A | 12/1911 | Lee | |
| 1,745,570 A | 2/1930 | Dimelow | |
| 1,772,027 A | 8/1930 | Baumgarten | |
| 1,780,117 A | 10/1930 | Craigo | |
| 2,031,996 A | 2/1936 | Zelesnick | |
| 2,398,671 A | 4/1946 | Saffir | |
| 2,585,857 A | 2/1952 | Schwartz | |
| 2,842,845 A | 7/1958 | Carlson | |
| 3,436,827 A | * 4/1969 | Dew | |
| 3,453,736 A | 7/1969 | Waltke | |
| 3,478,428 A | 11/1969 | Stengel | |
| 3,495,333 A | * 2/1970 | Kuhn | |
| 3,518,761 A | 7/1970 | Susman et al. | |
| 3,581,398 A | 6/1971 | Thomas | |
| 3,702,027 A | * 11/1972 | Marshall et al. | |
| 3,934,348 A | 1/1976 | Janjic | |
| 3,937,773 A | 2/1976 | Huffman | |
| 3,969,820 A | 7/1976 | Kulig et al. | |
| 4,021,916 A | 5/1977 | Spalten | |
| 4,022,419 A | 5/1977 | Haker | |
| 4,116,416 A | 9/1978 | Segura | |
| 4,122,606 A | 10/1978 | Roman | |
| 4,127,939 A | 12/1978 | Samuel et al. | |
| 4,203,219 A | 5/1980 | Wiener | |
| 4,240,605 A | 12/1980 | Waltke | |
| 4,242,812 A | 1/1981 | Randoll et al. | |
| 4,265,619 A | 5/1981 | Lucki et al. | |
| 4,283,173 A | 8/1981 | Browne et al. | |
| 4,301,357 A | 11/1981 | Huffman | |
| 4,359,464 A | 11/1982 | Weinstock | |
| 4,371,339 A | 2/1983 | Zeiser | |
| 4,378,929 A | 4/1983 | Huffman | |
| 4,382,787 A | 5/1983 | Huffman | |
| 4,398,884 A | 8/1983 | Huffman | |
| 4,439,151 A | 3/1984 | Whelan | |
| 4,443,192 A | 4/1984 | Blitz | |
| 4,449,930 A | 5/1984 | Huffman | |
| 4,449,931 A | 5/1984 | Saito | |
| 4,459,110 A | 7/1984 | Jackson | |
| 4,473,353 A | 9/1984 | Greggs | |

(Continued)

FOREIGN PATENT DOCUMENTS

DE 3 436 094 A1 10/1984

(Continued)

*Primary Examiner*—Ralph A. Lewis
(74) *Attorney, Agent, or Firm*—Merchant & Gould P.C.

(57) ABSTRACT

A dental model base having a cast stone core and method for making same. The stone core is cast within an encasement member. The encasement member is adapted for connection to an articulator.

22 Claims, 11 Drawing Sheets

U.S. PATENT DOCUMENTS

| | | |
|---|---|---|
| 4,481,162 A | 11/1984 | Huffman |
| 4,494,934 A | 1/1985 | Huffman |
| 4,521,188 A | 6/1985 | Metzler |
| 4,533,323 A | 8/1985 | Huffman |
| 4,538,987 A | 9/1985 | Weissman |
| 4,548,581 A | 10/1985 | Huffman |
| D283,541 S | 4/1986 | Huffman |
| D283,542 S | 4/1986 | Huffman |
| D283,639 S | 4/1986 | Huffman |
| D283,730 S | 5/1986 | Huffman |
| 4,608,016 A | 8/1986 | Zeiser |
| D286,179 S | 10/1986 | Huffman |
| D286,436 S | 10/1986 | Huffman |
| 4,645,454 A | 2/1987 | Amdur et al. |
| D289,924 S | 5/1987 | Huffman |
| 4,671,770 A | 6/1987 | Bell et al. |
| 4,708,648 A | 11/1987 | Weissman |
| 4,708,835 A | 11/1987 | Kiefer |
| 4,721,464 A | 1/1988 | Roden et al. |
| 4,734,033 A | 3/1988 | Huffman |
| 4,767,330 A | 8/1988 | Burger |
| 4,767,331 A | 8/1988 | Hoe |
| 4,834,651 A | 5/1989 | Fenick |
| 4,842,242 A | 6/1989 | Huffman |
| D302,456 S | 7/1989 | Huffman |
| D302,587 S | 8/1989 | Huffman |
| D302,724 S | 8/1989 | Huffman |
| D302,725 S | 8/1989 | Huffman |
| RE33,099 E | 10/1989 | Shoher et al. |
| D305,361 S | 1/1990 | Huffman |
| D305,362 S | 1/1990 | Huffman |
| D306,206 S | 2/1990 | Huffman |
| 4,898,359 A | 2/1990 | Gopon |
| RE33,271 E | 7/1990 | Shoher et al. |
| 4,940,409 A | 7/1990 | Nordin |
| 4,957,435 A * | 9/1990 | Jinoian et al. ........... 433/34 |
| 4,980,124 A | 12/1990 | Dimmer |
| 5,028,235 A | 7/1991 | Smith |
| 5,049,075 A | 9/1991 | Barrut |
| 5,076,789 A | 12/1991 | Tanaka |
| 5,098,290 A | 3/1992 | Honstein et al. |
| 5,100,317 A * | 3/1992 | Darnand ............... 433/60 |
| 5,197,874 A | 3/1993 | Silva et al. |
| 5,207,574 A | 5/1993 | Garland |
| 5,306,145 A * | 4/1994 | Michael ................ 433/34 |
| 5,352,117 A | 10/1994 | Silva |
| 5,393,227 A | 2/1995 | Nooning |
| 5,466,152 A | 11/1995 | Walter |
| 5,470,231 A | 11/1995 | Stern |
| 5,501,600 A | 3/1996 | Johnson |
| 5,506,095 A * | 4/1996 | Callne ................ 433/34 |
| 5,766,007 A | 6/1998 | Huffman |
| 5,769,634 A | 6/1998 | Choi |
| 5,775,899 A | 7/1998 | Huffman |
| 5,788,489 A | 8/1998 | Huffman |
| 5,788,490 A | 8/1998 | Huffman |
| 5,800,166 A | 9/1998 | Huffman |
| 5,807,099 A | 9/1998 | Johnson |
| 5,868,569 A | 2/1999 | Huffman |
| 5,996,963 A * | 12/1999 | Michael ................ 433/34 |
| 6,089,863 A | 7/2000 | Van Valey |
| D429,815 S | 8/2000 | Huffman |
| 6,099,305 A * | 8/2000 | Browne et al. ......... 433/34 |
| D430,672 S | 9/2000 | Huffman |

FOREIGN PATENT DOCUMENTS

| | | |
|---|---|---|
| DE | 3 505 680 A1 | 7/1985 |
| DE | 3 521 137 A1 | 12/1986 |
| DE | 3 825 014 A1 | 1/1990 |
| DE | 199 14 705 A1 | 5/2000 |
| EP | 0 210 484 A2 | 2/1985 |
| EP | 0 151 086 A2 | 8/1985 |
| EP | 0 277 026 A2 | 8/1988 |
| EP | 0 291 821 A1 | 11/1988 |
| EP | 0 528 335 A1 | 2/1993 |
| FR | 2 750 851 A1 | 1/1998 |
| GB | 866118 | 4/1961 |
| GB | 886118 | 1/1962 |
| WO | WO 88/ 10101 | 12/1988 |
| WO | WO 01/01881 A2 | 1/2001 |

* cited by examiner

ENCASED STONE DENTAL MODEL BASE BODY AND METHOD

FIELD OF THE INVENTION

The invention relates generally to a dental model base body, and specifically to a base body formed by pouring casting material into a cavity defined by a plurality of walls. Once cured, the casting material, together with the walls of the cavity, form the base body.

BACKGROUND OF THE INVENTION

Damaged teeth may be repaired or replaced by crowns, bridge inlays, porcelain veneer or other common dental prosthesis. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity outside the patient's mouth before the prosthesis is applied to the patient.

The model is typically formed by having a patient bite into a pliant casting material which cures to create a mold cavity having a negative impression of the patient's teeth and gums. The mold can be of all or any portion of the patient's gum line. A castable material is then poured into the negative impression to create a stone replica or dental model of the patient's teeth and gums, or a portion thereof. Once the castable material has cured, the mold is removed from the stone replica.

The dental model is typically connected to a base. Once connected to the base, the dental model may be cut and portions corresponding to damaged teeth may be removed and prosthesis fitted to the model of the damaged teeth. Once the prosthesis is fitted on a damaged tooth model, the damaged tooth model may be returned to the dental model base and alignment with adjacent teeth verified. Typically a model of the upper teeth is connected to a model of the corresponding lower teeth through their respective bases and an articulator. The articulator permits the technician to check the alignment of the prosthesis with opposing teeth. If the prosthesis does not align properly, the model of the damaged teeth may be removed and the prosthesis adjusted.

Dental model bases may be formed of plastic. Often, however, the dental model base is formed from a casting material. When a cast base is used, pins are fixed to the dental model. The pins protrude from the surface of the dental model that contacts the base. The pins may correspond to the teeth for which prosthesis are desired. The dental model is positioned adjacent a dental model base mold filled with uncured casting material. The pins protruding from the dental model extend into the uncured casting material. As the casting material cures, apertures are formed where the pins displace the casting material. After the casting material has cured, the base is removed from the mold. When the base has cured, the portions of the dental model corresponding to the pins may be disengaged from the base giving the technician access to the model of the damaged tooth. The detached segment may then be returned to the base and the pin reengage the aperture formed in the dental model base, assuring proper alignment with the dental model attached to the base.

Prior art bases used a relatively large quantity of casting material to support the dental model. Much of the casting material was required to give the base rigidity and stability. Casting material must be cured before it can be removed from the mold. Some distortions may result from the shrinkage associated with the curing of the casting material.

The cast base may have a slot formed in its anterior face to permit attachment to an articulator, such as the Vertex® articulator. Cast bases may also be attached to metal articulators by placing the side opposite the dental model adjacent the articulator and applying plaster to temporarily fix the cast dental model base to the articulator. Once the plaster cures, the dental model base is rigidly attached to the articulator.

SUMMARY OF THE INVENTION

The present invention is directed to an apparatus and method that provides an improved dental model base having a preformed outer wall and a cast core. The invention provides the advantages of a cast base while improving the quality of the resulting dental model base body. The invention also saves time and casting material as less casting material is used, which requires less time to cure and results in less distortion. Also, a separate mold is not required as the mold becomes part of the dental model base.

One embodiment of the invention comprises a stone member having a shape that at least generally corresponds to at least a portion of a patient's gum line. The stone member is molded within an encasement member. The encasement member includes structure that fixedly connects the stone member to the encasement member.

Another embodiment of the present invention is a dental model base encasement member. The member has a dental model support surface, a wall extending from the dental model support surface that is generally perpendicular to the dental model support surface. The wall has an exterior and interior surface. The interior surface of the wall defines a cavity that generally corresponds to the curvature of a gum.

Another embodiment of the present invention is a dental model and base. In this embodiment, a stone base supports a casting of a patient's teeth. The stone base is surrounded at least partially by an encasement member.

Another embodiment of the present invention is an encasement member. The encasement member has a dental model support surface, an opposing surface remote from the dental model support surface and a wall extending from the dental model support surface to the opposing surface. The wall has an interior surface and an exterior surface. The wall interior surface forms a cavity adapted to receive uncured casting material.

Another embodiment of the present invention is a system for connecting a dental model to an articulator. In this embodiment, an encasement member forms a cavity adapted to receive uncured casting material and an articulator attachment plate is connectable to the encasement member and to an articulator.

Another embodiment of the present invention is a system for connecting a dental model to an articulator. In this embodiment, an encasement member forms a cavity adapted to receive uncured casting material and a ball and socket connector is adapted to connect the encasement member to the articulator.

Another embodiment of the invention is a method for forming a dental model and base assembly. In this embodiment, a cavity formed by an encasement member is filled with uncured casting material. When the casting material cures, it is rigidly connected to the encasement member and the encasement member and the cured casting material form a dental model base. A dental model is placed adjacent the uncured casting material in the cavity. The dental model has at least one pin extending into the uncured casting material. When the casting material cures, it is engaged with the dental model base.

Another embodiment of the invention is a method of attaching a dental model to an articulator. In this method, a cavity formed within an encasement member is filled with casting material. A dental model is placed adjacent the uncured casting material in the cavity. The dental model has at least one pin extending into the uncured casting material. When the casting material is cured, the dental model is engaged with the casting material. A spherical connector that is connected to an articulator is mated with a concave portion of the base wall at a first end of the encased member.

One embodiment of the claimed invention is a method of attaching a dental model to an articulator. A cavity formed by an encasement member is filled with casting material. A dental model is placed adjacent the uncured casting material. When the casting material cures, the dental model is engaged to the casting material. A spherical connecter on an articulator attachment plate engages a concave portion of the base wall at a first end of the encasement member. The attachment plate is rotated until a latch on the plate engages a latch receiver at the second end of the encasement member. The attached plate is connected to an articulator.

In yet another embodiment, a cavity formed by an encasement member is filled with uncured casting material and a dental model is placed adjacent the uncured casting material. When the casting material cures, the model is engaged with the casting material. The encasement member is then connected to an articulator.

DETAILED DESCRIPTION OF PREFERRED EMBODIMENTS

Figure 1:
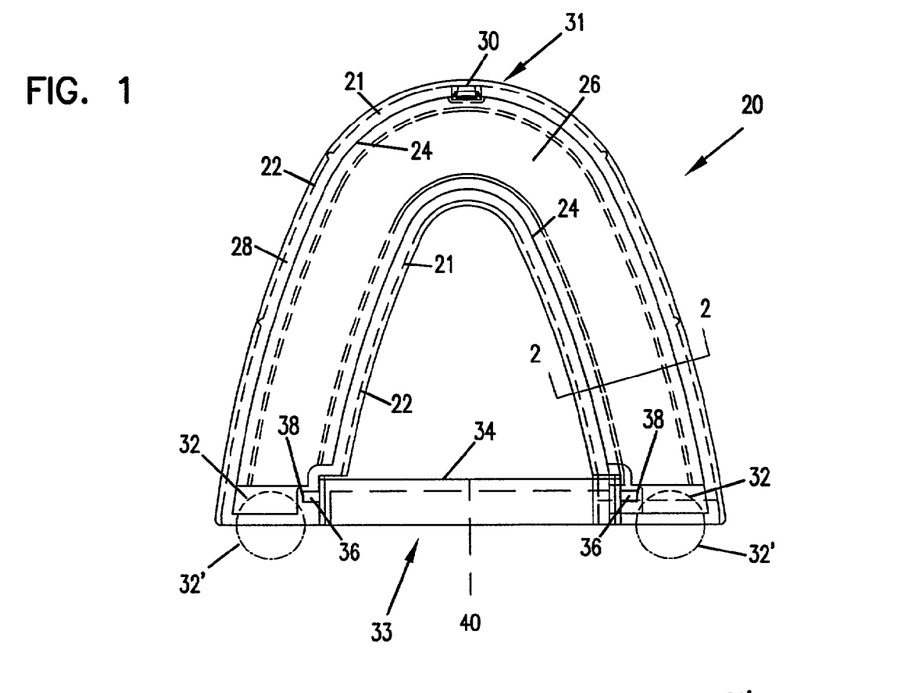
FIG. 1 is a plan view of an embodiment of an encasement member for use with a full arch model.

FIG. 1 depicts a plan view of the dental model encasement member 20. The encasement member has a wall 21 including an exterior surface 22 and an interior surface 24. The interior surface 24 of the wall 21 defines a cavity 26. The cavity follows generally the curvature of a patient's gum line. By analyzing tooth placement on a sampling of gum lines, the inventor has ascertained that three sets of encasement members will correspond generally to the gum lines of most Caucasian patients. A large, medium and small encasement member will correspond to the upper gum line, and a small, medium and large encasement member will correspond generally to the lower gum line. An example of the typical Caucasian tooth placement and gum line is provided in U.S. Pat. No. 5,788,489. Tooth placement and gum curvature for non-Caucasian populations may be found by simply analyzing samplings of that population. Similarly, tooth placement and gum curvatures for Caucasian gum lines other than what the inventor classifies as an upper medium may be found by analyzing samplings of dental models from a Caucasian population.

The encasement member 20 depicted in FIG. 1 is designed to fit an upper medium gum line. One end of the encasement member wall 21 includes a dental model support surface 28 that extends around a perimeter of the cavity 26. A latch receiver 30 is located at the anterior end 31 of the encasement member 20. The encasement member 20 also has hemispheric cavities 32 (shown in FIGS. 1 and 4) at its posterior end 33. In alternate embodiments, the hemispheric cavities 32 can be replaced with hemispheric projections 32' (shown in phantom line).

Figure 4:
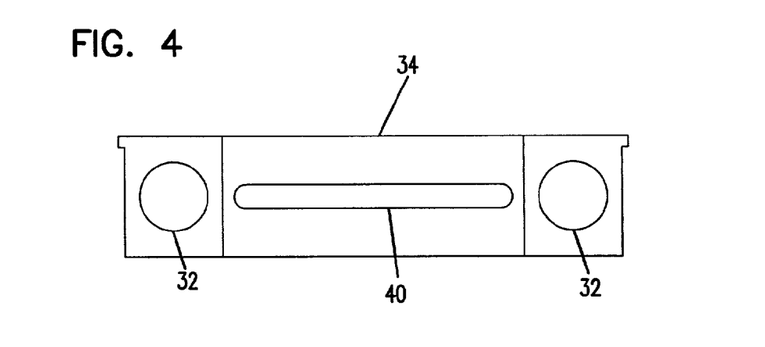
FIG. 4 is an end view of an encasement member.

In one embodiment, as depicted in FIG. 1 and FIG. 4, the posterior end of the encasement member 20 can be configured to facilitate connection to an articulator. For example, the posterior end can be shaped to receive an articulator attachment bar 34 having tongues 36 that slide into slots 38 in the posterior end of the encasement member 20. The articulator attachment bar 34 is shown defining an articulator engagement slot 40 adapted to receive a mating portion of an articulator to provide a connection therebetween. It will be appreciated that other structures such as slots, notches, projections, connectors, adhesive, etc. can be used to provide a connection between the encasement member and an articulator.

Figure 2:
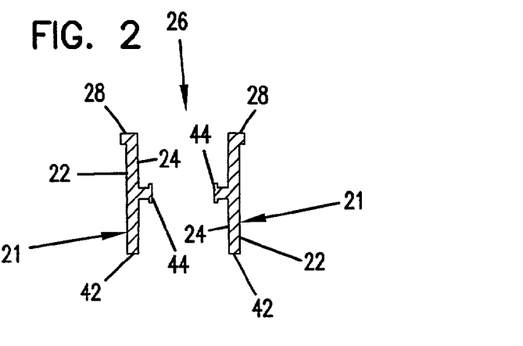
FIG. 2 is a cross-sectional view taken along section line 2—2 of FIG. 1.

FIG. 2 depicts a cross-section taken through line 2—2 of encasement member 20. The encasement member has an articulator attachment plate surface 42 opposite the dental model support surface 28. In the embodiment depicted, locking flange 44 protrudes from the interior surface 24 of the encasement member wall 21 midway between the dental model support surface 28 and the articulator attachment plate surface 42. Locking flange 44 extends along interior surface 24 for the entire length of cavity 26. In one embodiment, the interior surface above the locking flange tapers slightly outwardly (e.g., at a one degree angle) as it approaches the dental model support surface 28. Likewise, the interior surface 24 below locking flange 44 tapers slightly outwardly (e.g., at a one degree angle) as it approaches the articulator attachment plate surface 42. In the embodiment depicted, the distance from the dental model support surface 28 in the articulator attachment plate surface 42 is 0.66 inches. This height accommodates most commercially available pins used in dental modeling.

Figure 3:
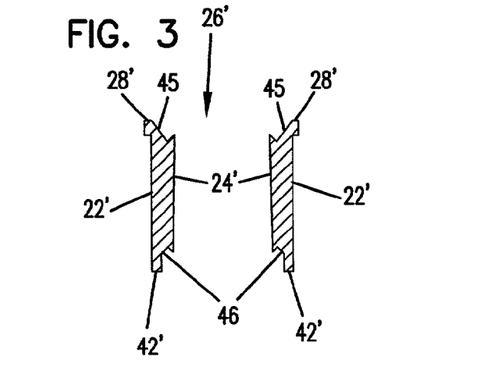
FIG. 3 is a cross-sectional view of an embodiment of an encasement member.

FIG. 3 represents a cross-sectional view of an alternate embodiment to the present invention. In this embodiment, locking flange 44 is eliminated. Interior surface 24' is shortened in this embodiment. The interior surface 24' is joined to the exterior surface 22' at dental model support surface 28' by a dental model support surface notch 45. The interior surface 24' is joined to the exterior surface 22' at articulator attachment plate surface 42' by an articulator attachment plate surface notch 46. The dental model support surface notch 45 and the articulator attachment plate surface notch 46 serve to engage the encasement member with the cured casting material. It will be appreciated that other configurations of notches or projections could also be used to provide structure for holding a cured casting member within cavity 26'.

Figure 5:
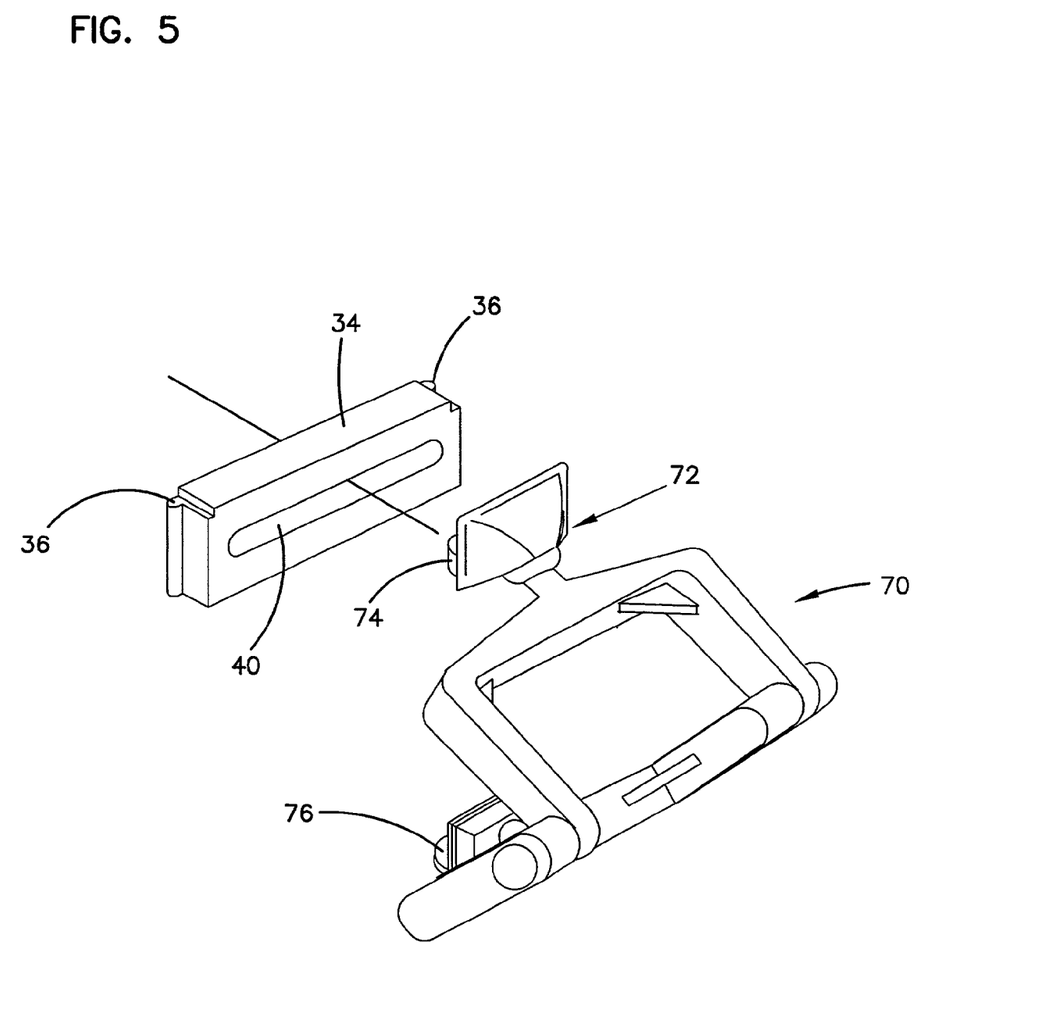
FIG. 5 is a perspective view of a prior art disposable articulator and an articulator attachment bar.

FIG. 5 illustrates a method of attaching a prior art disposable articulator with an embodiment of the present invention. The prior art articulator, known as a Vertex® articulator 70, has a ball and socket joint 72 that connects an articulator attachment tongue 74 to the articulator 70. The articulator attachment tongue 74 may engage the articulator engagement slot 40 on the articulator attachment bar 34 once the dental model connected to the attached encasement member 20 is properly aligned with an opposing dental model. The articulator attachment tongue 74 may be glued within the articulator engagement slot 40 and the ball and socket joint 72 may also be glued. Thereafter, the articulator 70 may be used as in known in the art to check for proper alignment on the dental model.

Figure 6:
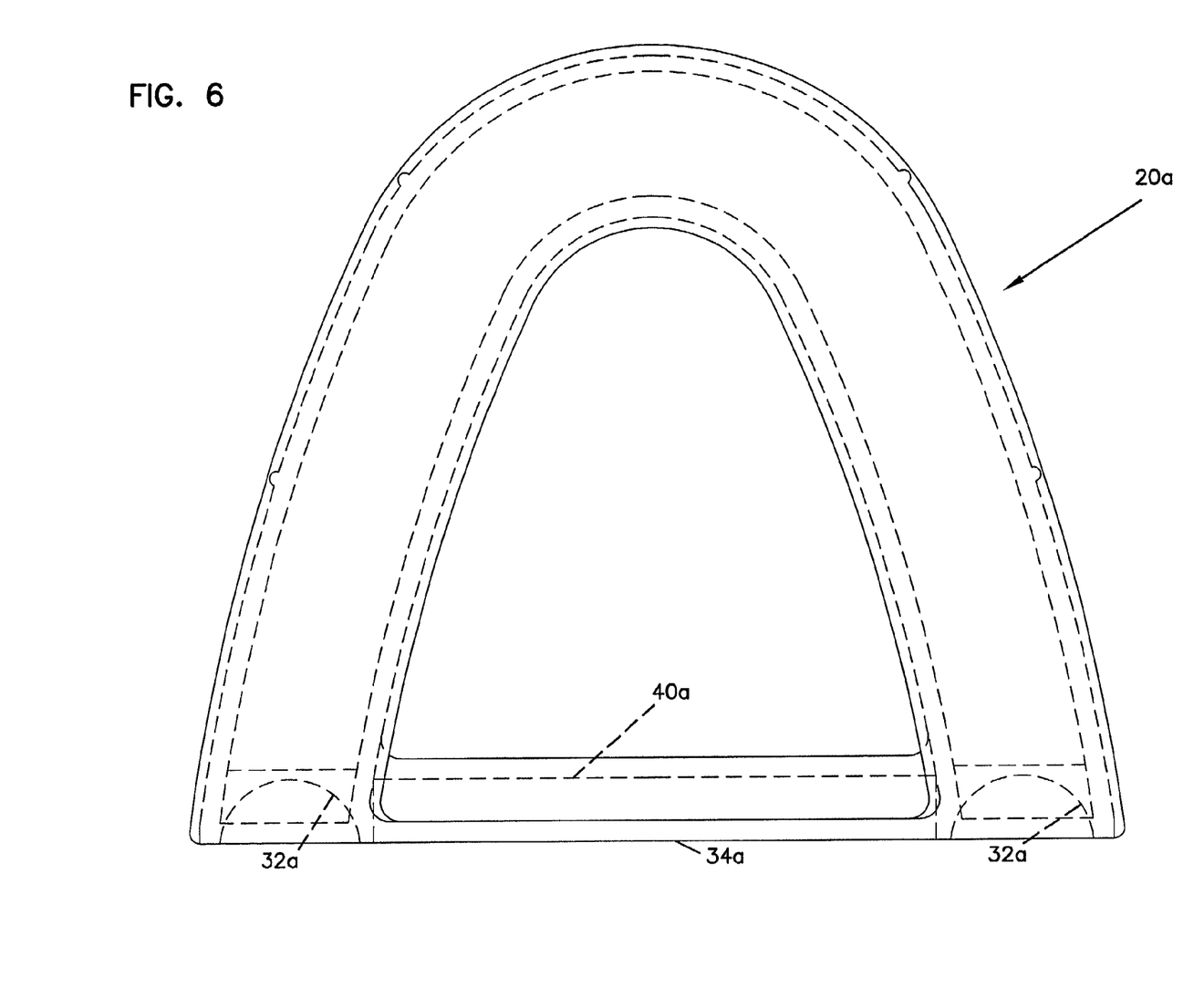
FIG. 6 is a plan view of an encasement member.
Figure 7:
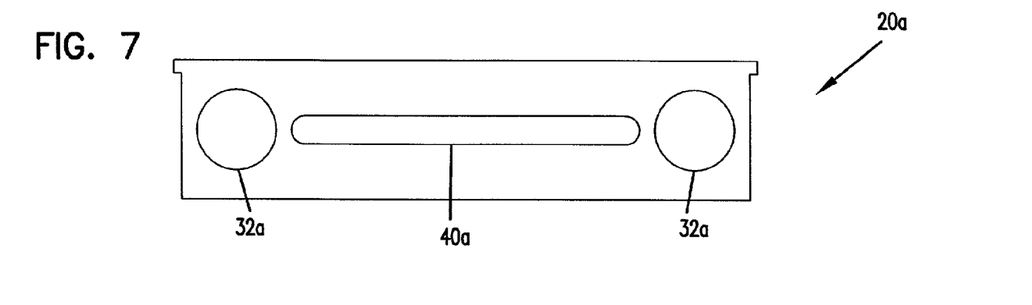
FIG. 7 is an end view of an encasement member.

FIGS. 6 and 7 depict an alternative embodiment of the present invention. In this embodiment, articulator attachment bar 34a is formed as an integral part of the encasement member 20a. FIG. 7 is again a posterior view of the encasement member 20a and depicts an articulator engagement slot 40a interposed between hemispheric cavities 32a.

Figures 8, 9:
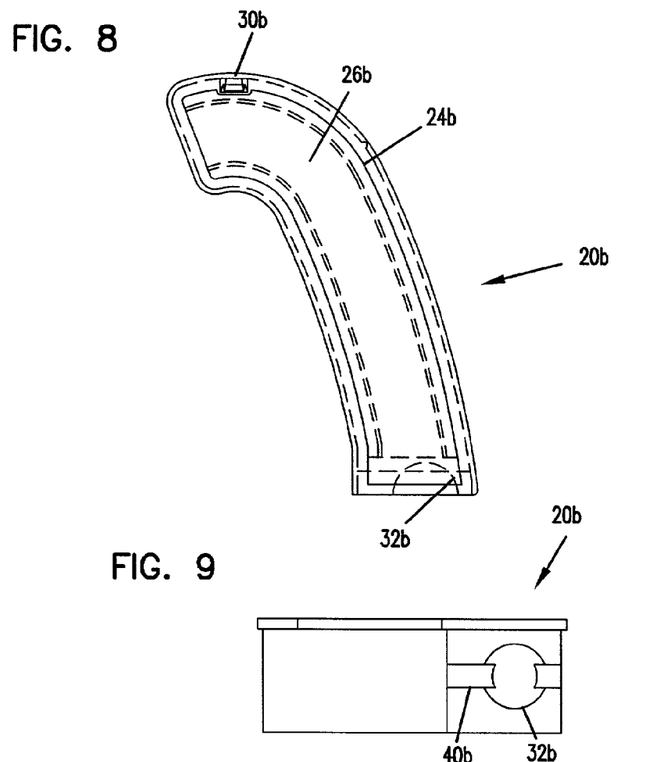
FIG. 8 is a plan view of an encasement member for a quadrant model.
FIG. 9 is an end view of an encasement member quadrant model.

FIG. 8 depicts an embodiment of the present invention adapted for use on a quadrant dental model. Encasement member 20b has a cavity 26b defined by interior surface 24b that generally follows the curvature of a patient's gum line. At the posterior end of the encasement member 20b is a hemispheric cavity 32b. At the anterior end of encasement member 20b is a latch receiver 30b.

FIG. 9 is a posterior view of the encasement member 20b. A slot 40b extends across the hemispheric cavity 32b on the posterior end of the encasement member 20b. Slot 40b is adapted to receive an articulator attachment tongue 74 as depicted in FIG. 5. Alternatively, the socket portion of the ball and socket joint 72 of articulator 70 may be discarded and the ball of that joint may be inserted directly into the hemispheric cavity 32b and glued in place once proper alignment has been achieved between the dental models supported by the articulator.

Figure 10:
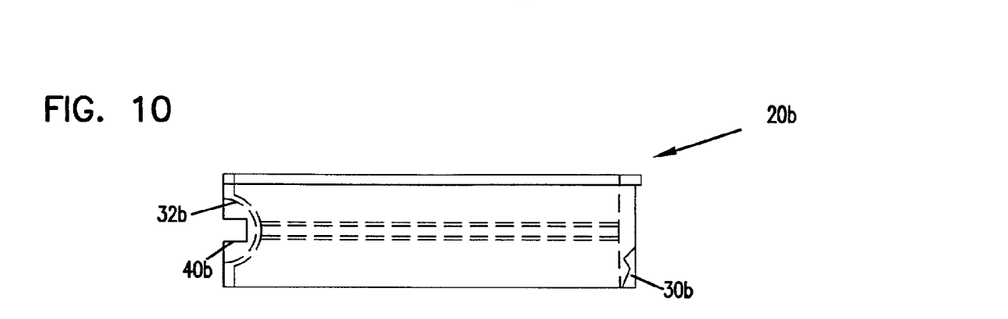
FIG. 10 is a side view of an encasement member for a quadrant model.

FIG. 10 is a side view of the encasement member 20b and depicts the latch receiver 30b at the anterior end of the encasement member 20b and the hemispheric cavity 32b at the posterior end of the encasement member 20b. Also depicted is slot 40b which extends across cavity 32b at the posterior end of the encasement member 20b.

Figure 11:
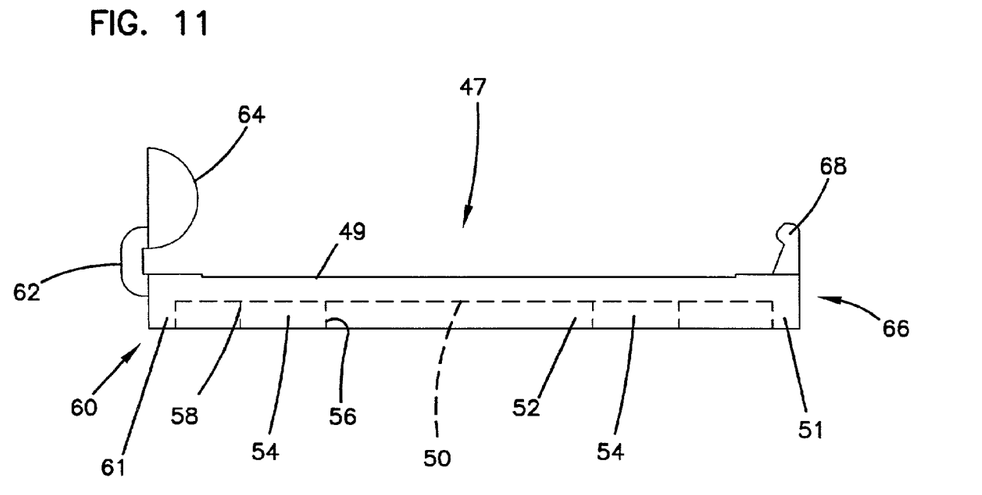
FIG. 11 is a side view of an articulator attachment plate.
Figure 12:
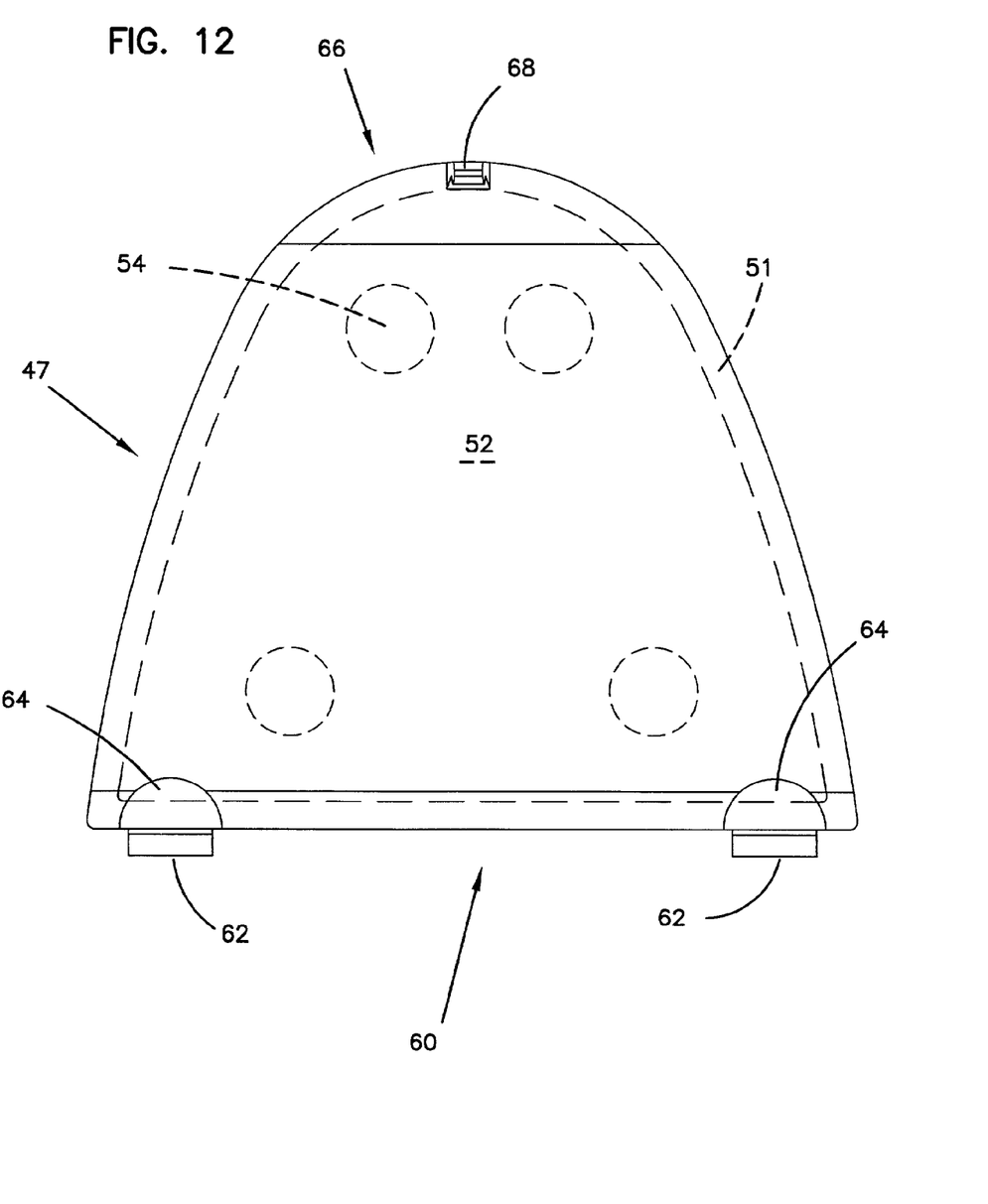
FIG. 12 is a plan view of an articulator attachment plate.

FIG. 11 depicts an articulator attachment plate 47 that provides an alternative technique for connecting the encasement member 20 to an articulator. The articulator attachment plate 47 has a dental model base engagement surface 49. Opposite the dental model base engagement surface 49 is an articulator attachment surface 50. An articulator attachment surface wall 51 projects outwardly from the articulator attachment surface 50, and extends about the perimeter of the attachment plate 46 to form an articulator attachment surface cavity 52. A plurality of anchors 54 also project outwardly from the attachment surface 50. The anchors 54 are located within the cavity 52 and are integrally formed with the attachment surface 50. The anchors 54 have anchor walls 56 that are tapered such that the anchor is narrower at its base 58 than at the anchor surface remote from the anchor base 58. FIG. 12 is a plan view of the articulator attachment plate 46 that better illustrates wall 51 around cavity 52, and also depicts the placement of anchors 54 within cavity 52.

One embodiment of the attachment plate 47 includes structure for providing a snap-fit connection with the encasement member 20. While any number of snap-fit configurations could be used, one embodiment includes a spring member 62 that connects a hemispheric member 64 with the attachment plate 47. The spring member 62 is located at a posterior end 60 of the attachment plate 47. At an anterior end 66 of the articulator attachment plate 47 is a latch 68.

Figure 15:
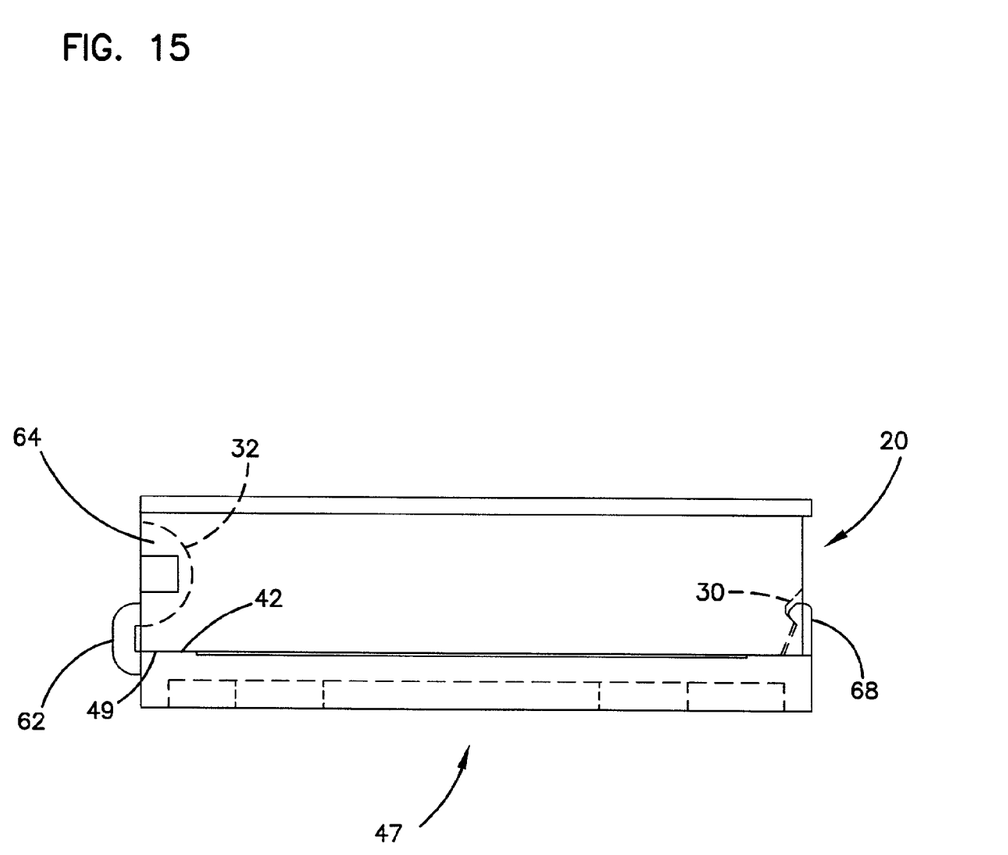
FIG. 15 is a side view of an articulator attachment plate engaging an encasement member.

FIG. 15 depicts the articulator attachment plate 47 mounted on the encasement member 20. As shown, hemispheric members 64 are positioned within the cavities 32, and latch 68 is interlocked with receiver 30. A transparent material can be used for the encasement member 20 and for the articulator attachment plate 47. Clear plastics may be used such as polycarbonate plastics commonly known as Lexan.

Figure 13:
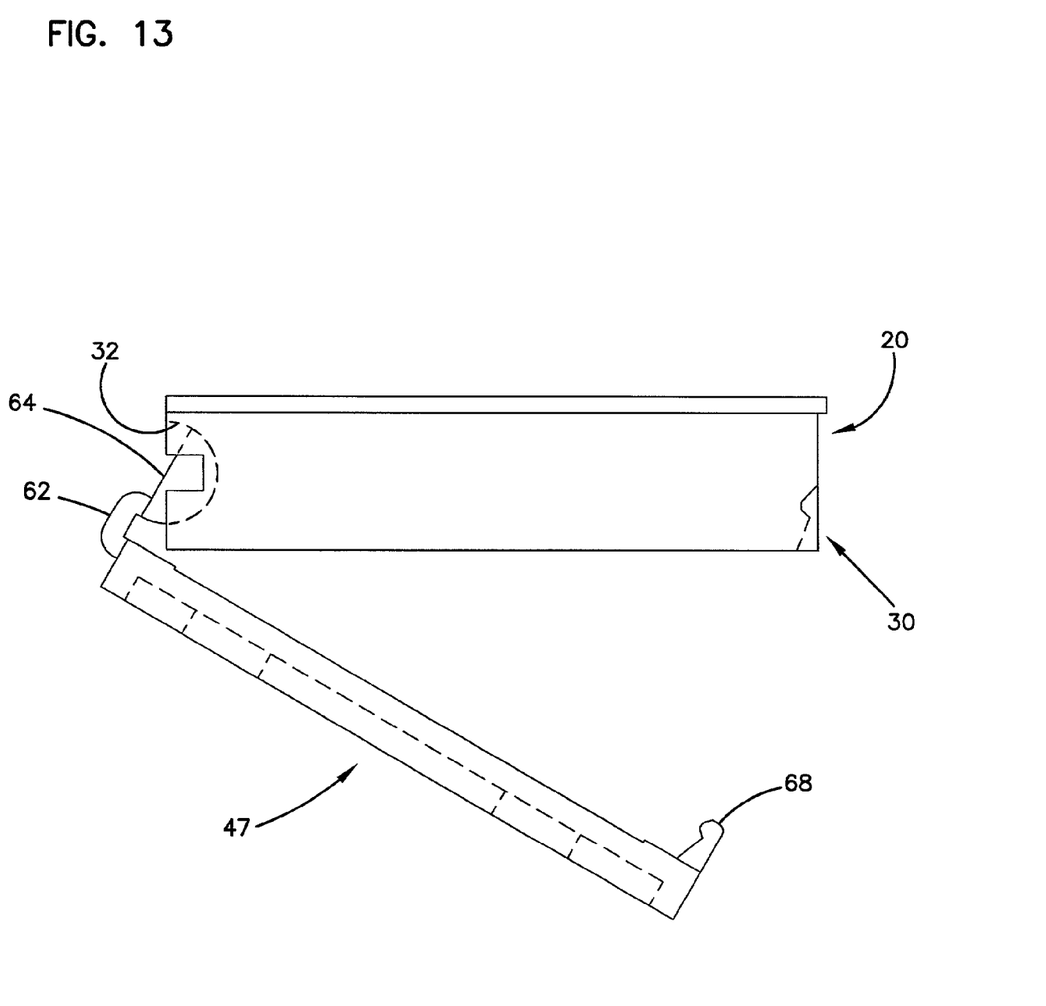
FIG. 13 is a side view of an articulator attachment plate engaging an encasement member.
Figure 14:
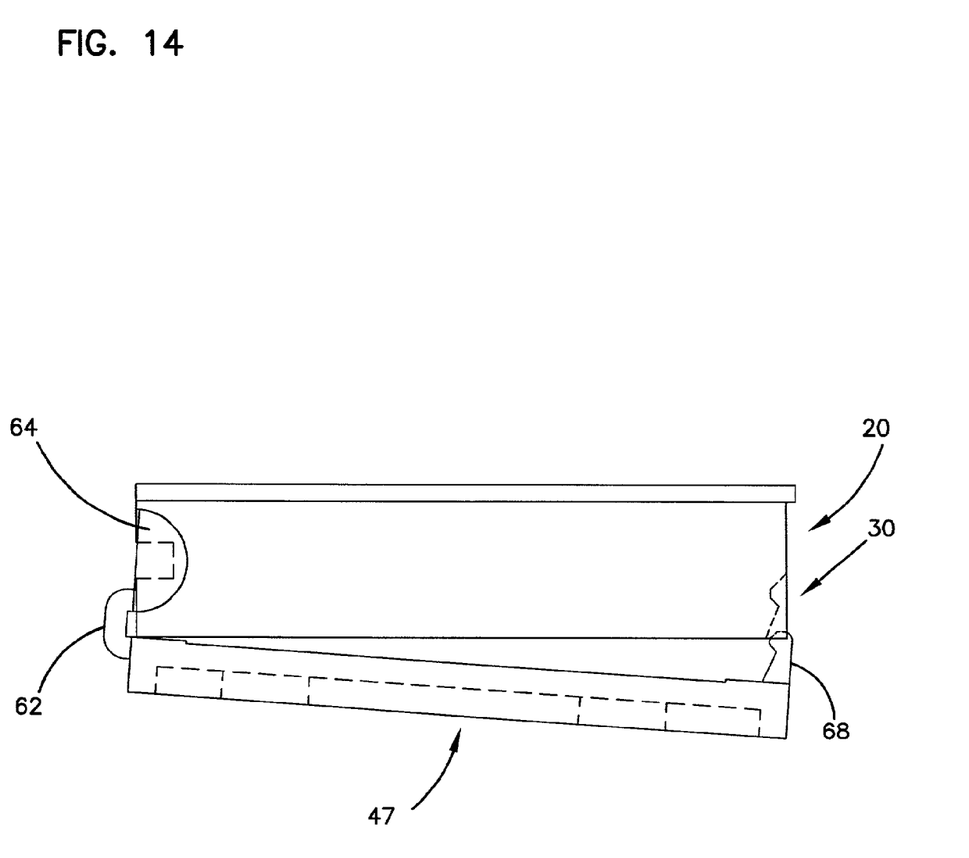
FIG. 14 is a side view of an articulator attachment plate engaging an encasement member.

FIGS. 13–15 sequentially shown the attachment plate 47 being connected to the encasement member 20. FIG. 13 depicts the articulator attachment plate 47 being engaged with the encasement member 20. As depicted in FIG. 14, latch 68 has begun to engage receiver 30 which causes spring member 62 to flex slightly. FIG. 15 depicts the articulator attachment plate 47 in complete engagement with encasement member 20. As shown, latch 68 has slid past a notch in receiver 30 and the tension in the spring member 62 is now somewhat relaxed and the articulator attachment plate 47 is firmly engaged with the encasement member 20. As shown, the articulator attachment plate surface 42 of the encasement member 20 opposes the dental model base engagement surface 49 of the plate 47.

In operation, the articulator attachment plate 47 is placed adjacent a metal articulator and is plastered in position adjacent the articulator (e.g., the articulator can be connected to the articulator attachment surface 50). The encasement member 20 may then be connected to the articulator through the articulator attachment plate 47 by simply engaging the hemispheric cavity of the encasement member with the hemispheric member of the attachment plate and rotating the attachment plate such that the latch engages the latch receiver as depicted in FIGS. 13–15. Once the encasement member and attached dental model are connected to the articulator, the technician may use the articulator as is known in the art for alignment. Alternatively, disposable articulators may be used to assess the registration or alignment of the prosthesis.

Figure 16:
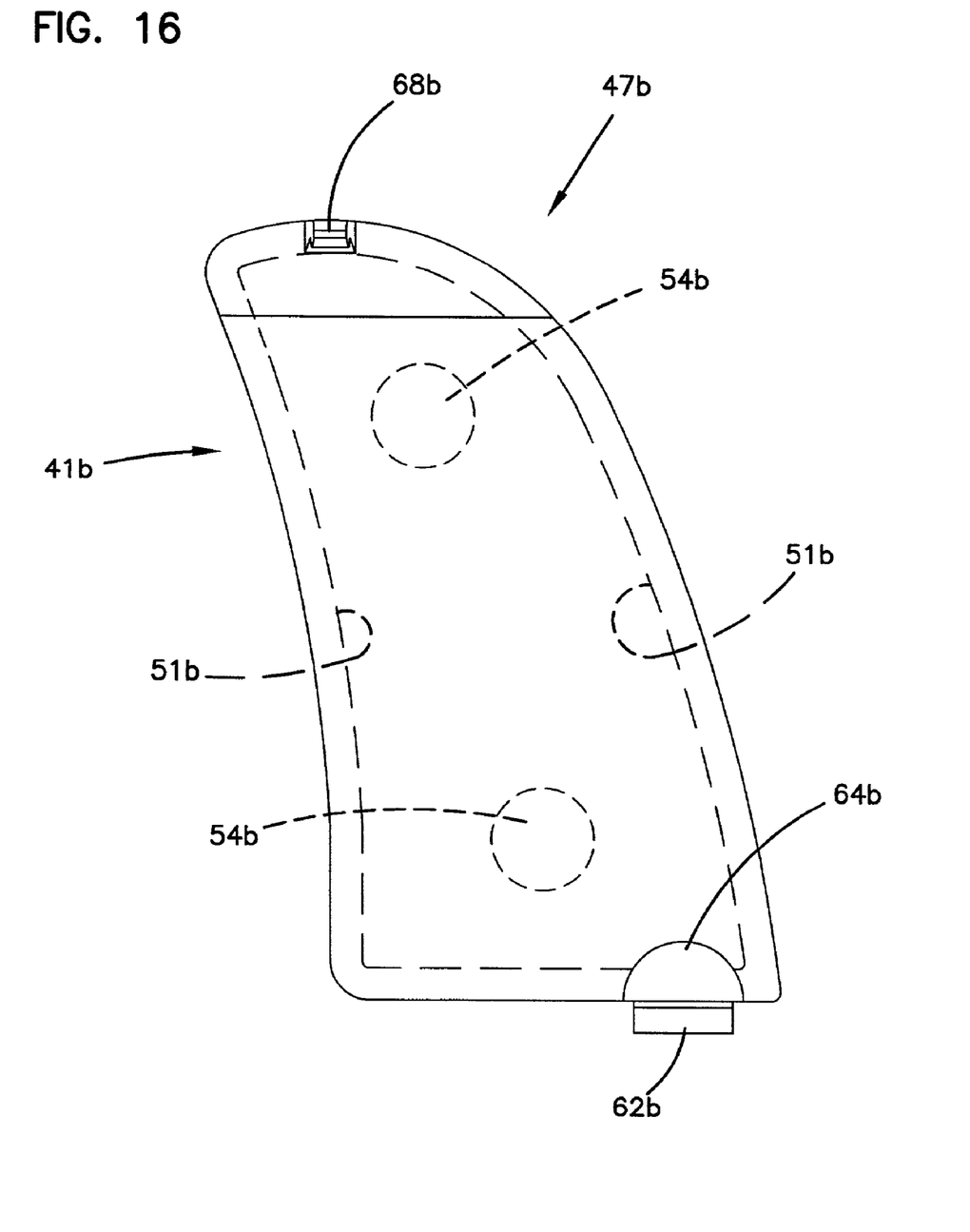
FIG. 16 is a plan view of an articulator attachment plate for a quadrant encasement member.

FIG. 16 is a plan view of an articulator attachment plate 47b adapted for use with a quadrant model. Attachment plate 47b has an attachment plate wall 51b that defines the cavity 52b. Inside the cavity are anchors 54b. At the posterior end of the attachment plate 47b is hemispheric member 64b that is attached to the articulator attachment plate 47b by a spring member 62b. At the anterior end of the articulator attachment plate is a latch 68b.

Figure 17:
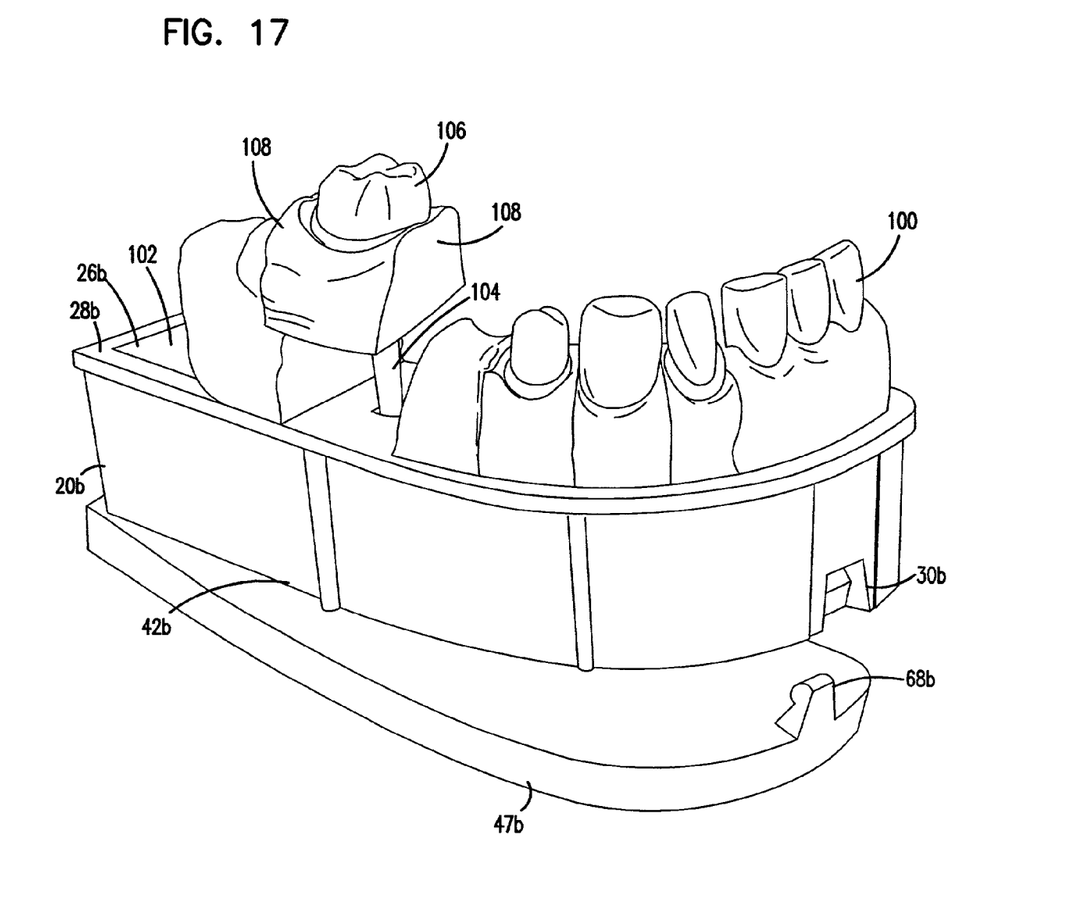
FIG. 17 is a perspective view of an encasement member supporting a dental model and being attached to an attachment plate.

FIG. 17 is a perspective view of a dental model 100 attached to an encased stone member 102 that is cast within encasement member 20b. The articulator attachment plate 47b is shown connected to the encasement member 20b. The assembly is prepared as follows: the articulator attachment plate 47b is connected to the encasement member 20b with the latch 68b firmly engaging the latch receiver 30b.

Uncured casting material is poured into the gum-line shaped cavity 26*b* formed by the encasement member 20*b*. Preferably, tapered pins 104 were previously affixed to the cast dental model 100 of the patient's gum. In one embodiment, the pins are stainless steel and have a 2 percent taper with a 0.005 inch tolerance and a 20 micron finish. The dental model 100 and protruding pins 104 are placed adjacent the uncured casting material contained within the cavity 26*b* of the encasement member 20*b* with the pins 104 protruding into the uncured casting material. Typically, a pin 104 is placed at least below the tooth 106 for which a prosthetic is required.

Once the casting material has cured, the model of the damaged tooth 106 may be removed from the model of the gum by using a saw to provide a cut 108 on each side of the model of the damaged tooth 106. The saw cut ends at the top of the encasement member 20*b*. The pin 104 is typically shorter than the distance from the dental model support surface 28*b* to the articulator attachment plate surface 42*b* of the encasement member 20*b*. As is known in the prior art, the cured casting material on the articulator attachment plate side of the encasement member may be removed to expose the end of the pin. Access to the articulator attachment plate side of the encasement member 20*b* can be provided by removing plate 46*b*. Once the pin end is uncovered, pressure may be applied to the pin to force the models of the damaged tooth 106 from the dental model 100.

After the model of the damaged tooth 106 is removed, the technician may prepare the desired prosthesis and return the model of the damaged tooth with the prosthesis to the dental model 100 to check for alignment. Many methods for assuring proper alignment of the model of the damaged tooth with the dental model base are known in the prior art. For example, dummy pins may be used or pins with a flat surface on one side may be used, or the base of the dental model may be scored such that a groove is formed and when the dental model is mated to the uncured casting material, a ridge will be formed in the casting material to mate with the groove in the dental model.

Once the model of the damaged tooth 106 is returned to the dental model 100, the dental model 100 may be connected to an articulator to check for alignment of the applied prosthesis with the opposing dental model.

The foregoing describes various embodiments of the claimed invention. The claimed inventions are not limited to the embodiments described above. For example, numerous shapes could be used for the encasement member. Various additional methods of attaching the encased base to an articulator will also be apparent to one skilled in the art.

What is claimed is:

1. A method for forming a dental model and base assembly comprising:
    filling a cavity defined by a single piece encasement member with uncured casting material; the encasement member including an engagement structure extending into the cavity that engages the casting material in said cavity such that the cured casting material is fixed to the encasement member; said encasement member and cured casting material forming a dental model base; and
    placing a cast dental model adjacent said uncured casting material in said cavity; said dental model being engaged with said dental model base when said casting material is cured;
    wherein a pin is connected to said cast dental model and said pin extends into said uncured casting material when said dental model is placed adjacent said uncured casting material in said cavity.

2. The method of claim 1 wherein said encasement member forms a ball and socket joint with an articulator.

3. The method of claim 1 wherein said encasement member detachably engages with an articulator attachment plate and said articulator attachment plate being adapted to be connected to an articulator.

4. The method of claim 1 wherein said encasement member has a slot at a first end; said slot adapted for receiving an articulator attachment tongue.

5. The method of claim 4 wherein said slot is formed in an articulator attachment bar that slidingly engages the encasement member first end.

6. The method of claim 1, wherein said engagement structure includes at least one slanted surface that extends at an angle relative to a plane defined by a top surface of the dental model base upon which the cast dental model is placed.

7. The method of claim 1, wherein said engagement structure includes at least one undercut structure to fix the cured casting material to the encasement member.

8. The method of claim 1, further comprising coupling the encasement member to an articulator attachment plate, wherein the attachment plate extends along a bottom surface of the encasement member and is coupled to the encasement member with a ball and socket and latch connection.

9. A method of attaching a dental model to an articulator comprising:
    filling a cavity formed by an encasement member with uncured casting material;
    placing a dental model adjacent said uncured casting material in said cavity; said dental model having at least one pin extending into said uncured casting material; said dental model being engaged with said casting material when said casting material is cured;
    engaging a spherical connector with a concave portion of said encasement member; said spherical connector being connected to an articulator.

10. The method of claim 9 wherein:
    said spherical connector is glued into position after engaging the concave portion of said encasement member.

11. The method of claim 10 wherein said spherical connector is connected to a plastic articulator.

12. The method of claim 9 further comprising coupling an articulator attachment plate between the encasement member and the articulator.

13. The method of claim 9 wherein said encasement member detachably engages with an articulator attachment plate and said articulator attachment plate is adapted to be connected to the articulator.

14. The method of claim 9 wherein said encasement member has a slot defined at a first end, said slot adapted for receiving an attachment tongue of the articulator.

15. The method of claim 14 wherein said slot is formed in an articulator attachment bar that slidingly engages the encasement member first end.

16. The method of claim 9, wherein said encasement member includes an engagement structure extending into the cavity that engages the casting material in said cavity.

17. The method claim 16, wherein said engagement structure includes at least one slanted surface that extends at an angle relative to a plane defined by a top surface of the dental model base upon which the cast dental model is placed.

18. The method of claim 16, wherein said engagement structure includes at least one undercut structure to fix the cured casting material to the encasement member.

19. The method of claim 9, further comprising coupling the encasement member to an articulator attachment plate, wherein the attachment plate extends along a bottom surface of the encasement member and is coupled to the encasement member with a ball and socket and latch connection.

20. A method of attaching a dental model to an articulator comprising:
filling a cavity formed by an encasement member with uncured casting material;
placing a dental model adjacent said uncured casting material in said cavity; curing said casting material so that said dental model is engaged with said casting material when said casting material is cured;
engaging a spherical connector with a concave portion provided at a first end of said encasement member; said spherical connector being at a first end of an articulator attachment plate;
rotating said articulator attachment plate around said concave portion of said encasement member until a latch on a second end of said articulator attachment plate engages a latch receiver at a second end of said encasement member; and
attaching said articulator attachment plate to an articulator.

21. The method of claim 20, further comprising coupling at least one pin member between the dental model and the casting material in the cavity.

22. The method of claim 20, wherein the encasement member includes an engagement structure that protrudes into the cavity for engagement by the casting material.

* * * * *